United States Patent [19]

Pharr et al.

[11] Patent Number: 5,268,288
[45] Date of Patent: Dec. 7, 1993

[54] MANNITOL OXIDOREDUCTASE ISOLATED FROM VASCULAR PLANTS

[75] Inventors: David M. Pharr; Johan M. H. Stoop, both of Raleigh, N.C.

[73] Assignee: North Carolina State University, Raleigh, N.C.

[21] Appl. No.: 857,388

[22] Filed: Mar. 25, 1992

[51] Int. Cl.$^5$ .......................... C12N 9/04; C12N 5/00
[52] U.S. Cl. .................................. 435/190; 435/240.4
[58] Field of Search ............................ 435/190, 240.4

[56] References Cited

U.S. PATENT DOCUMENTS 4,927,752 5/1990 Remacle .................................. 435/8

OTHER PUBLICATIONS

M. Tarczynski et al., *Plant Physiol.* (Supplement) 889, 133 (1991).

J. Everard and W. Loescher, *Plant Physiol.* (Supplement) 4, 2 (1991).

R. Broglie et al., *Plant Molecular Biology* 3, 431–444 (1984).

P. Trip et al., *Amer. Jour. Bot.* 51, No. 8, 828–835 (1964).

Grant & Hackh's chemical dictionary, p. 214, 1987, Fifth edition.

*Primary Examiner*—David M. Naff
*Assistant Examiner*—Michael V. Meller
*Attorney, Agent, or Firm*—Bell, Seltzer, Park & Gibson

[57] ABSTRACT

A mannitol oxidoreductase is isolated from vascular plants which is NAD$^+$ dependent and which converts mannitol to mannose. A preferred source of the mannitol oxidoreductase is *Apium graveolens*, particularly *Apium graveolens* L. var. *rapaceum* (Mill.) Gaud. (celeriac) and *Apium graveolens* L. var. *dulce* (Mill.) Pers. (celery). DNA encoding of the mannitol oxidoreductase may be used in the production of the enzyme.

7 Claims, 9 Drawing Sheets

FIG.7

MANNITOL OXIDOREDUCTASE ISOLATED FROM VASCULAR PLANTS

FIELD OF THE INVENTION

The present invention relates to mannitol oxidoreductases in general, and particularly relates to the discovery of an NAD+-dependent mannitol: mannose 1-oxidoreductase which can be isolated from vascular plants.

BACKGROUND OF THE INVENTION

Mannitol is by far the most abundant polyol in nature, occurring in bacteria, fungi, algae, lichens and vascular plants. See R. Bieleski, in: *Encyclopedia of Plant Physiology*, New Series Volume 13A. *Plant Carbohydrates I*. p.158-192 (1982); D. Lewis, in: *Storage carbohydrates in vascular plants. Distribution, physiology and metabolism*. p.158-179 (1984). Although several physiological roles have been proposed for mannitol, such as carbohydrate storage, regulation of carbon partitioning, osmoregulation and cofactor regulation, little information exists on the enzymatic pathways of mannitol synthesis and utilization. See R. Bieleski, supra; W. Loescher, *Physiol. Plantarum* 70:553-557 (1987); M. Rumpho et al., *Plant Physiol.* 73:869-873 (1983). Most information has come from studies of fungi and bacteria which contain a mannitol dehydrogenase that catalyzes the NAD-dependent or NADP dependent oxidation of D-mannitol to D-fructose. See, e.g., D. Quain et al., *J. Gen. Microbiol.* 133:1675-1684 (1987); W. Niehaus et al., *Mycopathologia* 107:131-137 (1989).

NAD-dependent mannitol-1-P dehydrogenase has been detected in bacteria, brown algae and fungi which catalyzes the conversion of mannitol-1-P to fructose-6-P. See, e.g., S. Horwitz et al., *J. Biol. Chem.* 239: 830-838 (1964); Richter and Kirst, *Planta* 170:528-534 (1987); R. Kiser et al., *Arch. Biochem. Biophys.* 211:613-621 (1981). All three enzymes are 2-oxidoreductases and can catalyze the reaction in either direction, toward synthesis or utilization of the polyol depending on the availability of oxidized or reduced cofactor and the pH.

Mannitol catabolism in higher plants is still poorly understood. Several labeling studies using [$^{14}$C]-mannitol suggest that mannitol is utilized at a slow rate in vascular plants. When celery leaf discs were incubated in [$^{14}$C]-mannitol, mannitol utilization was restricted to young leaf tissue. See J. Fellmann et al., *Physiol. Plantarum* 69:337-341 (1987). Suspension cultures of *Daucus carota* L. and *Pinus radiata* D. or carrot root tissue had a small uptake and metabolism of [$^{14}$C]-mannitol. See M. Thompson et al., *Physiol. Plant.* 67:365-369 (1986); W. Cram, *Physiol. Plant.* 61:396-404 (1984). Mannitol respiration, as measured by [$1<CO_2$] evolution, was monitored in fifteen higher plant species and ranged from very low rates (*Avena sativa*) to rates comparable to that of fructose or glucose (*Fraxinus americana*). White ash leaflets exposed to [$^{14}$C]-mannitol resulted in the formation of a small amount of [$^{14}$C]-fructose after 2 days, perhaps suggesting that the first step of mannitol utilization in this species may be oxidation to fructose. See P. Trip et al., *Amer. Jour. Bot.* 51:828-835 (1964). Although these labeling studies support the presence of a mannitol utilizing enzyme in higher plants, insofar as we are aware, no mannitol oxidizing enzyme has been isolated from a vascular plant.

SUMMARY OF THE INVENTION

The present invention is based upon our discovery of a mannitol oxidoreductase in celeriac and celery. Insofar as we are aware, this represents the first report of the existence of a mannitol: mannose 1-oxidoreductase in any living organism.

A first aspect of the present invention is isolated NAD+-dependent mannitol: mannose 1-oxidoreductase (mannitol oxidoreductase; mannitol dehydrogenase). The mannitol oxidoreductase may be obtained from plants, with a preferred source being *Apium graveolens*.

A second aspect of the present invention is isolated DNA encoding NAD+-dependent mannitol: mannose 1-oxidoreductase (mannitol oxidoreductase), as given above. In one embodiment, the isolated DNA is selected from the group consisting of: (a) isolated DNA which encodes *Apium graveolens* mannitol oxidoreductase; (b) isolated DNA which hybridizes to isolated DNA of (a) above and which encodes a mannitol oxidoreductase as given above; and (c) isolated DNA differing from the isolated DNAs of (a) and (b) above in nucleotide sequence due to the degeneracy of the genetic code, and which encodes a mannitol oxidoreductase as given above.

Other aspects of the invention include vector DNA comprising a DNA sequence encoding a promoter operative in a plant cell operatively associated with NAD+-dependent mannitol: mannose 1-oxidoreductase (mannitol oxidoreductase), along with plants transformed with such a vector.

Mannitol oxidoreductase of the present invention is useful for converting mannitol (not digestible by humans) to mannose, which may then be further converted to other types of sugars by known enzymes. DNA encoding mannitol oxidoreductase is useful for genetically engineering plants which contain mannitol to convert that mannitol to mannose with the mannose then optionally being converted to other sugars by endogenous enzymes or enzymes introduced into that plant by genetic engineering techniques.

The foregoing and other objects and aspects of the present invention are explained in detail in the drawings herein and the specification below.

BRIEF DESCRIPTION OF THE DRAWINGS

FIG. 1 shows the hexose (A), sucrose (B) and mannitol (C) concentration of stressed celeriac cv. Monarch plants. Plants were transferred to 8" pots at week zero. Carbohydrate analysis was done at time of transfer (week zero) and one week after transfer (week one).

FIG. 2 shows the mannitol (A), sucrose (B) and hexose (C) concentration of different plant parts of celeriac cv. Monarch. (YP, young petiole; YL, young leaf; MP, mature petiole; ML, mature leaf; SI, innermost part of stem; TRI, innermost part of tap root; OR, older root; RT, root tip).

FIG. 5 shows the kinetic parameters of mannitol dehydrogenase of celeriac root tips (S=mannitol). Top: substrate saturation curves at pH 9.0 (A) and pH 7.5 (B). Bottom: Lineweaver-Burk plots at pH 9.0 (C) and pH 7.5 (D).

FIG. 6 shows the kinetic parameters of mannitol dehydrogenase of celeriac root tips (S=NAD). Top: substrate saturation curves at pH 9.0 (A) and pH 7.5 (B); bottom: Lineweaver-Burk plots at pH 9.0 (C) and pH 7.5 (D).

DETAILED DESCRIPTION OF THE INVENTION

The term "plant" herein refers to higher plants (i.e., vascular plants). Mannitol oxidoreductase of the present invention may be that of any plant, including both gymnosperms and angiosperms (including both monocots and dicots). Preferred sources are plants which have been reported to contain mannitol, and particularly preferred sources are plants which have been reported to both contain and utilize mannitol. Numerous such plants are known. See, e.g., S. Barker, in *Modern Methods of Plant Analysis*, Vol. 2, p. 62-67 (K. Paech and M. Tracev eds. 1955); E. Bourne, in *Encyclopedia of Plant Physiology* 6: 345-372 (1958); A. Cranswick and J. Zabkiewicz, *J. Chromatography* (1979); M. Thompson et al., *Physiol. Plant.* 67: 365-369 (1986); P. Trip et al., *Amer. Jour. Bot.* 51: 828-835 (1964); M. Zimmermann and H. Ziegler, in *Encyclopedia of Plant Physiology*, Vol. 1, New-Series, pp. 408-503 (1975).

Plants reported to contain mannitol include the following: *Apium graveolens* L. var. rapaceum (Mill.) Gaud. (celeriac); *Apium graveolens* L. var dulce (Mill.) Pers. (celery); *Daucus carota* L. (carrot); *Oenanthe crocata; Oenanthe crocata; Pastinaca sativa* L. (parsnip, wild p.); *Cocus nucifera* L. (coconut); *Scorzonera hispanica* L. (black salsify); *Brassica oleracea* L. Botrytis group (cauliflower); *Brassica oleracea* L. Capitata group (cabbage); *Ananas comosa* (L.) Merr (pineapple); *Buxus sempervitens* L. common boxwood); *Opuntia vulgaris* Mill; *Canella alba* Murr.; *Laguncularia racemosa* (L.) Gaertn. f. (white mangrove); *Terminalia arjuna Bedd; Terminalia chebula* (Gaertn.) Retz.; *Terminalia myriocarpa* Heurck et Muell.-Arg.; *Terminalia oliveri* Brandis; *Lactuca sativa* L. (lettuce); *Ipomaea purga* (Wender.) Hayne. (jalap); *Citrillus vulgaris* (watermelon); *Cucurbita pepo* L. (pumpkin, squashes); *Manihot utilissima* Pohl (cassava, manioc); *Cercis siliquastrum* L.; *Glycyrhiza glabra* L. (common licorice); *Gymnocladus canadensis* L.; *Phaseolus vulgaris* L. (green bean, French bean); *Pisum* (pea); *Spartium junceum* L. (Spanish broom); *Ephedra distachya; Agropyron repens; Andropogon annulatus; Asparagus offinalis* L. (asparagus); *Forestiera acuminata* (Michx.) Poir. (swamp privet); *Forestiera neomexicana; Fraxinus americana* L. (white ash); *Fraxinus exelsior* L. (European ash); *Fraxinus julandifolia; Fraxinus oregona* Nutt. var. glabra; *Fraxinus ornus* L. (flowering ash, manna); *Fraxinus oxycarpa* Willd.; *Fraxinus pistaciaefolia; Fraxinus rotundifolia; Jasminum abyssinicum; Jasminum beesianum; Jasminum fruticans; Jasminum heterophyllum; Jasminum humile; Jasminum nudiflorum* Lindl. (winter jasmine); *Jasminum odoratissimum; Jasminum officinale* L. (poet's jessamine); *Ligustrum ibota; Ligustrum japonicum* Thunb.; *Ligustrum vulgare* L. (common privet); *Olea europaea* L. (olive); *Olea glandulifera; Olea lancea; Osmanthus aquifolium; Osmanthus armatus; Osmanthus jragrans; Syringa amurensis; Syringa emodii; Syringa julianae* Schr.; *Syringa pekinensis; Syringa persica; Syringa pubescens* Turcz.; *Syringa vulgaris* L. (common lilac); *Orobanche cumana; Orobanche ramosa* L. (hemp broomrape); *Pinus radiata* D. Don (Monterey pine); *Platanus orientalisn* L. (oriental planetree); *Cyclamen europaeum; Punica granutum* L. (pome granate); *Aconitum napellus* L. (aconite, monkshood); *Delphinium consolida; Prunus lauracerasus* L. (cherry, laurel); *Coffea arabica* L. (coffee); *Gardenia brasiliensis; Gardenia florida* L.; *Gardenia jasminoides* Ellis (Cape, jasmine); *Gardenia turgida; Linaria vulgaris* Mill. (yellow toadflax); and *Veronica* (speedwell). These species are representative of the following plant families: Apiaceae, Arecaceae, Asteraceae, Brassicaceae, Bromeliaceae, Buxaceae, Cactaceae, Canellaceae, Combretaceae, Compositae, Convolvulaceae, Cucurbitaceae, Cucurbita, Euphorbiaceae, Fabaceae, Gnetaceae, Gramineae, Liliaceae, Oleaceae, Orobanchaceae, Pinaceae, Platanaceae, Primulaceae, Punicaceae, Ranunculaceae, Rosaceae, Rubiacea, and Scrophulariaceae.

Plants reported to both contain and metabolize Mannitol include the following: *Apium graveolens* L. var. rapaceum (Mill.) Gaudich (celeriac); *Apium graveolens* L. var dulce (Mill.) Pers. (celery); *Brassica oleracea* L. Botrytis group (cauliflower); *Ananas comosa* (L.) Merr (pineapple); *Lactuca sativa* L. (lettuce); *Asparagus officinalis* L. (asparagus); *Fraxinus americana* L. (white ash); *Fraxinus ornus* L. (flowering ash, manna); *Ligustrum vulgare* L. (common privet): *Syringa vulgaris* L. (common lilac): *Coffea arabica* L. (coffee); and *Gardenia florida* L. These species are representative of the following families: Apiaceae, Brassicaceae, Bromeliaceae, Compositae, Liliaceae, Oleaceae, and Rubiacea.

Isolated mannitol oxidoreductase of the present invention may be produced in the manner described below, or variations thereof which will be apparent to those skilled in the art. In one embodiment, the isolated mannitol oxidoreductase is essentially free from alcohol dehydrogenase and phosphomannose isomerase. Isolated mannitol oxidoreductase of the invention [e.g., isolated *Apium graveolens* L. var. rapaceum (Mill.) Gaud. NAD+ dependent mannitol: mannose 1-oxidoreductase (celeriac mannitol oxidoreductase), as described below] is further purified, and/or purified sufficiently for amino acid sequencing, in accordance with known techniques, such as with high performance liquid chromatography (HPLC), affinity chromatography (e.g., with antibodies to the enzyme or with an NAD affinity column), comprehensive two-dimensional high performance liquid chromatography coupling ion exchange chromatography and size exclusion chromatography (see M. Bushey and J. Jorgenson, *Analytical Chemistry* 62: 161-167 (1990)), two-dimensional HPLC/Capillary zone electrophoresis (see, e.g., M. Bushey and J. Jorgenson, *Analytical Chemistry* 62: 978-984 (1990) and variations thereof (i.e., where other liquid chromatography columns such as reverse phase chromatography columns, ion exchange chromatography columns, adsorption chromatography columns, and affinity chromatography columns are used; or where other capillary electrophoresis apparatus such as capillary gel electrophoresis, capillary isotachophoresis, micellar electrokinetic capillary chromatography, and capillary isoelectric focusing are used), other multidimensional separation systems (see J. Giddings, *J. High Resolut. Chromatogr. Chromatogr. Commun.* 10:319-323 (1987)), SDS-polyacrylamide gel electrophoresis, two-dimensional polyacrylamide gel electrophoresis such as disclosed in R. Broglie et al., *Plant Mol. Biol.* 3:431-444 (1984), etc. Thus, the present invention provides isolated mannitol oxidoreductase having specific activities of 1, 10, 50, 100, or even 200 or more, in Units per Milligram of Protein, as described in greater detail below.

Isolated DNA encoding *Apium graveolens* mannitol oxidoreductase is produced from isolated *Apium graveolens* mannitol oxidoreductase in accordance with known techniques. Amino acid sequences or partial amino acid sequences are generated from isolated mannitol oxidoreductase in accordance with known techniques, such as the automated sequencing of tryptic digests of isolated mannitol oxidoreductase as described above. From the amino acid sequence or sequences, one or more degenerate oligonucleotide probes are generated and labelled and used to screen an appropriate DNA library (e.g., a genomic DNA library produced from a source which contains DNA encoding a mannitol oxidoreductase or a cDNA library produced from a suitable source enriched in mRNA encoding the mannitol oxidoreductase) to isolate a DNA sequence encoding a mannitol oxidoreductase of the invention. The construction of oligonucleotide probes, DNA libraries, and the hybridization screening of such DNA libraries with oligonucleotide probes is carried out in accordance with known techniques. See generally J. Sambrook et al., *Molecular Cloning: A Laboratory Manual* (2d ed. 1989)(Cold Spring Harbor Laboratory Press). In the alternative, PCR primers are generated from the amino acid sequences and used to either screen a DNA library directly or produce a larger oligonucleotide probe for use in screening a DNA library, also in accordance with known techniques, to isolate a DNA sequence encoding a mannitol oxidoreductase of the invention. See, e.g., U.S. Pat. No. 4,683,202 to Mullis and U.S. Pat. No. 4,683,195 to Mullis et al.

Isolated DNA encoding mannitol oxidoreductase may be obtained from isolated DNA encoding *Apium graveolens* mannitol oxidoreductase in accordance with known hybridization techniques. Thus, DNA sequences which hybridize to DNA which encodes mannitol oxidoreductase of the invention and which code on expression for a mannitol oxidoreductase of the invention are also an aspect of this invention. Conditions which will permit other DNA sequences which code on expression for a mannitol oxidoreductase of the invention to hybridize to the DNA sequence of *Apium graveolens* mannitol oxidoreductase (e.g., the DNA sequence encoding *Apium graveolens* L. var. rapaceum (Mill.) Gaud. (celeriac) or *Apium graveolens* L. var. dulce (Mill.) Pers. (celery) mannitol oxidoreductase) can be determined in a routine manner. For example, hybridization of such sequences may be carried out under conditions of reduced stringency or even stringent conditions (e.g., conditions represented by a wash stringency of 0.3M NaCl, 0.03M sodium citrate, 0.1% SDS at 60° C. or even 70° C. to DNA encoding *Apium graveolens* mannitol oxidoreductase in a standard in situ hybridization assay. See J. Sambrook et al., Molecular Cloning, A Laboratory Manual (2d Ed. 1989)). In general, sequences which code for a mannitol oxidoreductase of the invention and hybridize to the DNA encoding *Apium graveolens* mannitol oxidoreductase will be at least 75% homologous, 85% homologous, or even 90% homologous or more with the sequence of *Apium graveolens* mannitol oxidoreductase. Further, DNA sequences which code for *Apium graveolens* mannitol oxidoreductase, or sequences which code for a mannitol oxidoreductase coded for by a sequence which hybridizes to the DNA sequence which *Apium graveolens* mannitol oxidoreductase, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

Hybridization procedures are available which allow for the isolation of cDNA clones whose mRNA levels are as low as about 0.05% of poly(A+)RNA. See M. Conkling et al., *Plant Physiol.* 93, 1203-1211 (1990). In brief, cDNA libraries are screened using single-stranded cDNA probes of reverse transcribed mRNA from plant tissue (i.e., roots and leaves). For differential screening, a nitrocellulose or nylon membrane is soaked in 5×SSC, placed in a 96 well suction manifold, 150 µL of stationary overnight culture transferred from a master plate to each well, and vacuum applied until all liquid has passed through the filter. 150 µL of denaturing solution (0.5M NaOH, 1.5M NaCl) is placed in each well using a multiple pipetter and allowed to sit about 3 minutes. Suction is applied as above and the filter removed and neutralized in 0.5M Tris-HCl (pH 8.0), 1.5M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

The term "operatively associated," as used herein, refers to DNA sequences on a single DNA molecule which are associated so that the function of one is affected by the other. Thus, a promoter is operatively associated with a structural gene (i.e., a gene encoding mannitol oxidoreductase as given above) when it is capable of affecting the expression of that structural gene (i.e., the structural gene is under the transcriptional control of the promoter). The promoter is said to be "upstream" from the structural gene, which is in turn said to be "downstream" from the promoter.

Numerous promoters operable in plant cells are known which may be employed in practicing the present invention, including a broad variety of plant viral promoters and promoters associated with cloned plant genes, such the Cauliflower mosaic virus 35S promoter, inducible heat shock protein promoters such as the HSP 70 promoter, light inducible promoters such as the ribulose bisphosphate carboxylase small subunit promoter and the chlorophyll AB binding protein promoter, stress response proteins such as the PR protein promoter, the *Agrobacterium tumefaciens* nos promoter, and root-specific promoters such as those disclosed in R. Croy et al., PCT Application Publication Number WO91/13992, S. Gurr et al., *Mol. Gen. Genet.* 226: 361-366 (1991), and M. Conkling et al., *Plant Physiol.* 93: 1203-1211 (1990).

DNA constructs, or "expression cassettes," of the present invention include, 5'-3' in the direction of transcription, a promoter as discussed above, a structural gene operatively associated with the promoter, and, optionally, a termination sequence including a stop signal for RNA polymerase and a polyadenylation signal for polyadenylase (e.g., the nos terminator). All of these regulatory regions should be capable of operating in the cells of the tissue to be transformed. The 3' termination region may be derived from the same gene as the transcriptional initiation region or may be derived from a different gene.

Structural genes are those portions of genes which comprise a DNA segment coding for a mannitol oxidoreductase as given above, optionally including a ribosomal binding site and/or a translational start codon, but lacking a promoter. This term can also refer to copies of a structural gene naturally found within a cell but artificially introduced. The structural gene may encode a protein not normally found in the plant cell in which the gene is introduced or in combination with the promoter to which it is operationally associated, in which case it is termed a heterologous structural gene. Structural genes which may be operationally associated with a promoter of the present invention for expression in a plant species may be derived from a chromosomal gene, cDNA, a synthetic gene, or combinations thereof.

Where the expression product of the structural gene is to be located in a cellular compartment other than the cytoplasm, the structural gene may be constructed to include regions which code for particular amino acid sequences which result in translocation of the product to a particular site, such as the cell plasma membrane, or may be secreted into the periplasmic space or into the external environment of the cell. Various secretory leaders, membrane integration sequences, and translocation sequences for directing the peptide expression product to a particular site are described in the literature. See, for example, Cashmore et al., *Bio/Technology* 3, 803–808 (1985), Wickner and Lodish, *Science* 230, 400–407 (1985).

The expression cassette may be provided in a DNA construct which also has at least one replication system. For convenience, it is common to have a replication system functional in *Escherichia coli,* such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complementation, by imparting prototrophy to an auxotrophic host: or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase, providing indigo production, luciferase, providing visible light production, NPTII, providing kanamycin resistance or G418 resistance, HPT, providing hygromycin resistance, and the mutated aroA gene, providing glyphosate resistance.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Maniatis et al., Molecular Cloning: A Laboratory Manual, Cold Spring Harbor Laboratory, Cold Spring Harbor, N.Y., 1982.

Vectors which may be used to transform plant tissue with DNA constructs of the present invention include both Agrobacterium vectors and ballistic vectors, as well as vectors suitable for DNA-mediated transformation.

*Agrobacterium tumefaciens* cells containing a DNA construct of the present invention, wherein the DNA construct comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous Agrobacterium vector systems useful in carrying out the present invention are known. For example, U.S. Pat. No. 4,459,355 discloses a method for transforming susceptible plants with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles carrying a DNA construct of the present invention, which microparticles are suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050 (applicants intend that the disclosure of all U.S. Patent references cited herein be incorporated herein by reference), and in Agracetus European Patent Application Publication No. 0 270 356, titled *Pollen-mediated Plant Transformation.* When using ballistic transformation procedures, the expression cassette may be incorporated into a plasmid capable of replicating in the cell to be transformed. Examples of microparticles suitable for use in such systems include 1 to 5 μm gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

The present invention is explained in greater detail in the following non-limiting examples. In these examples, "ppm" means parts per million, "mM" means millimolar, "M" means Molar, "mA" means milliAmps, "ml" means milliliters, "µmol" means micromoles, "nm" means nanometers, "U" means units, "Mops" means 3-(N-Morpholino) propanesulfonic acid, "EDTA" means ethylenediaminetetraacetic acid, "DTT" means dithiothreitol, "h" means hours, "min." means minutes, "g" means gravity, "rpm" means revolutions per minute, "MDH" means mannitol dehydrogenase, and temperatures are given in degrees centigrade unless otherwise indicated.

EXAMPLE 1

Isolation of NAD+-Dependent Mannitol: Mannose Oxidoreductase

I. Materials and Method

A. Materials

Celeriac (*Apium graveolens* var. rapaceum) cultivar 'Monarch' was seeded and reached transplant stage approximately three months later. Some seedlings were kept in seeding flats (1" by 1" containers) for a period of 4 weeks, in order to intentionally stress the young plants before being transplanted to 8" pots. Celeriac cv. 'Marble Ball' transplants, acquired from DNA-Plant Technology Inc., were transplanted in 10" pots containing soilless media (Promix) and grown in a greenhouse for about five months. Plants were watered daily and fertilized twice a week with a soluble fertilizer solution (200 ppm N, 100 ppm $P_2O_5$, 200 ppm $K_2O$). Substrates and nucleotides were obtained from Sigma Chemical Co. or from Pharmacia Fine Chemical, Inc. Because the highest purity of mannitol obtained from Sigma Chemical Co. still contained ca. 1% sorbitol, mannitol was purified by two successive recrystilizations from $H_2O$ thereby eliminating sorbitol contamination in the mannito substrate.

B. Purification of mannitol:mannose 1-oxidoreductase

Enzyme extraction. Celeriac root tips were harvested, pooled and washed in distilled water. Fresh roots were ground in a chilled mortar using a 1:4 tissue-to-buffer ratio. Theextraction buffer contained 50 mM Mops (pH 7.5, 5 mM $MgCl_2$, 1 mM EDTA, 5 mM DTT and 1% Triton X-100. Homogenates were centrifuged at 20,000 g for 15 min at 4° C. The crude extract consisted of supernatant that was desalted by centrifugal filtration on a Sephadex G-25-50 column equilibrated with 50 mM Mops-NaOH (pH 7.5), 5 mM $MgCl_2$ and 5 mM DTT prior to assay for MDH activity.

Purification. Supernatant from the root extraction was brought to 45% saturation with ammonium sulfate at 4° C. and centrifuged at 20,000 g for 15 min. The supernatant was retained and brought to 65% saturation by further addition of $(NH_4)_2SO_4$. After centrifugation the supernatant was discarded and the pellet was suspended in a minimum volume of 20 mM Mops (pH 7.5), 2 mM $MgCl_2$ and 1 mM DTT. The dissolved pellet was filtered through a 0.4 µm filter and applied to a Fractogel ® DEAE ion-exchange column (10 cm × 1.5 cm) equilibrium with 20 mM Mops (pH 7.5), 2 mM $MgCl_2$ and 1 mM DTT. Protein eluting from the DEAE column was monitored by absorbance at 280 nm and protein in pooled fractions with Bio-Rad reagent. Proteins were eluted with a linear KCl salt gradient, 0M to 0.4M KCl, in running buffer. Flow rate equaled 1.25 ml/min. and two ml fractions were collected. Fractions containing MDH which was free from alcohol dehydrogenase (ADH) or phosphomannose isomerase (PMI) were pooled and further concentrated by ammonium sulfate precipitation (90% saturation), and the pellet was resuspended in a small volume of 20 mM Mops (pH 7.5), 2 mM $MgCl_2$ and 1 mM DTT. The concentrated enzyme was desalted and stored at −80° C.

C. Enzyme Assays

Spectrophotometric assay. Mannitol dehydrogenase (MDH) activity was assayed by monitoring the oxidation-reduction of NADH/NAD+ spectrophotometrically at 340 nm. Assays were done at 25° C. in a total volume of 1 ml. Optimum conditions (buffer, pH and substrate concs) were determined. The reaction mixture contained 100 mM Bis-Tris (pH 9.0), 2 mM NAD+, enzyme extract and 150 mM D-mannitol. The reactions were initiated with mannitol. One unit of activity was defined as the amount of enzyme which catalyzes the reduction of 1 µmol NAD+ per hour (µmol/h). For the reverse reaction (mannose reduction) the enzyme extract was incubated in a mixture 0.1 mM NADH, enzyme extract, 20 mM substrate (D-mannose, D-fructose or D-glucose) and 100 mM MOPS at pH=7.5 in a total volume of 1 ml.

The alcohol dehydrogenase (ADH) assay was similar to the MDH assay using 5 mM ethanol as the substrate. The phosphomannose isomerase (PMI) assay contained the following reaction mixture: 100 mM Hepes (pH 7.5), 2 mM NAD+, enzyme extract and 150 mM D-mannitol.

Detection of enzyme activity by staining. Enzyme extract was loaded on a 7.5% T, 2.6% C polyacrylamide gel, electrophoresed at constant voltage (200 V, 150 mA) for 40 to 45 min. on a Mini-Protean II gel apparatus and stained for MDH activity. MDH activity stain contained 50 ml of 0.2M Bis-Tris pH 9.0, 150 mM mannitol, 2 mM NAD+, 1 ml of MTT (3,(4,5-demethythiazolyl-2)-2,5-diphenyltetrazolium bromide Sigma) (10 mg/ml) and 0.5 ml of PMS (2 mg/ml) phenazine methosulphate (Sigma).

D. Product Purification and Identification

Four different MDH reactions either containing the complete reaction mixture (100 mM Bis-Tris (pH=9.0), 2 mM NAD+, 10 μl partially purified enzyme and 150 mM mannitol); the complete reaction (−mannitol); the complete reaction (−NAD+) or the complete reaction (−enzyme) extract were run for 2 hours, heat killed in boiling water for 60 seconds and centrifuged at 10,000 g for 1 min. Because the buffer in the reaction mixture co-chromatographed with and masked several sugars including mannose and fructose it was necessary to purify the reaction product away from its reaction buffer prior to analysis of the product on a HPLC system. An ion-exchange column was developed which was composed of an anion-exchanger (Bio-Rad AG 1-X8, H+-form) separated from a cation-exchanger (Dowex-50W, formate form) by Watman #1 paper. Total column volume equaled 2 ml. Columns were spun to dryness for 4 min. at 1,000 rpm in a table top centrifuge. When this column was loaded with 1 ml of MDH reaction mixture and centrifugally passed through, the column effectively exchanged the highly concentrated buffer, Bis-Tris, with a lower concentration of formic acid. The latter had the great advantage, that on the chromatogram, formic acid had a different retention time (RT=4.26 min.) than mannose (RT=11.20 min.) or fructose (RT=12.00 min.). When mannose was added to the MDH reaction mixture, loaded on the ion-exchange column and analyzed by HPLC on a Bio-Rad Fast Carbohydrate column (Pb column) a distinct mannose peak (RT=3.64 min.) could be observed. Because the Waters Sugar-Pak I column (Ca column) had much longer retention times (RT) for most of the sugars, the Fast Carbohydrate column with shorter RT values was used to hasten the process of product purification. The MDH product peak was collected from numerous injections, freeze dried and suspended in 1 ml of distilled $H_2O$.

The purified MDH product resulting from the protocol above was then analyzed on three different HPLC systems: 1) An HPLC system containing a Bio-Rad Fast Carbohydrate column (Pb column) 2) A HPLC system with high resolution conditions consisting of a Waters Sugar-Pak I calcium column which was not preceded by a Waters Bondapak C18/Corasil guard or anion and cation cartridges (Bio-Rad Laboratories). Elimination of the guards resulted in very high resolution chromatography with particular improvement in the resolution between mannose and fructose. 3) A Dionex High Performance Anion Exchange Chromatography system using pulsed amperometric detection. The purified product was also identified with an enzymatic link system using commercial reagent enzymes so that the presence of mannose could be differentiated from fructose. This enzymatically linked spectrophotometric assay consisted of 5 U/ml hexokinase, 0.047 U/ml phosphomannose isomerase, 1 U/ml phosphoglucoisomerase and 1 U/ml glucose-6-P dehydrogenase, 1 mM NAD+, 1 mM ATP, 1 mM MgCl, 100 mM MOPS buffer at pH=7.5 and was initiated with 20 μg/ml substrate (mannose, fructose or purified product). Assays were done at 25° C. in a total volume of 1 ml. The product determination is based ultimately on the Glucose-6-P dehydrogenase reaction which reduces NAD+ to NADH and can be monitored spectrophotometrically at 340 nm. The key enzyme for mannose detection is phosphomannose isomerase (PMI). By comparing the amount of NAD+ reduction in the presence (+PMI) and absence (−PMI), it is possible to determine if fructose or mannose is present in a particular sample. If mannose is the sample, the (−PMI) reaction will exhibit no NAD+ reduction while the (+PMI) will. If both (+PMI) and (−PMI) result in equal NAD reduction fructose and or glucose is in the sample.

E. Carbohydrate Analysis

Ethanolic extractions from each of the samples were used for measurements of sucrose, hexose sugars and polyols. The procedures for ethanolic extraction were followed as described by N. Hubbard et al., *Plants Physiol.* 91:1527-15 (1989). Carbohydrate content was determined on a HPLC system using a Waters Sugar-Pak I (Ca column). The column was preceded by a Waters Bondapak C18/Corasil guard and a set of anion and cation cartridges (Bio-rad Laboratories).

II. Results

Figure 1A:
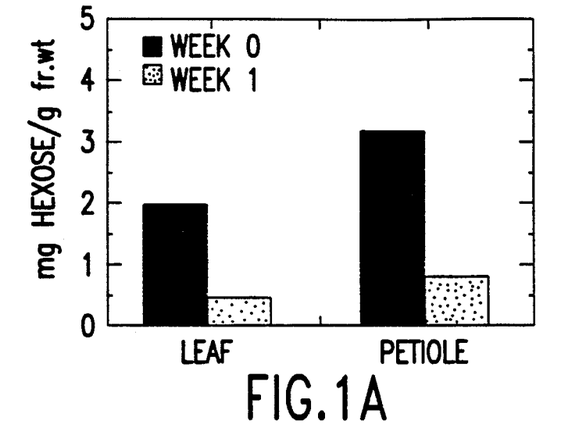
Figure 1B:
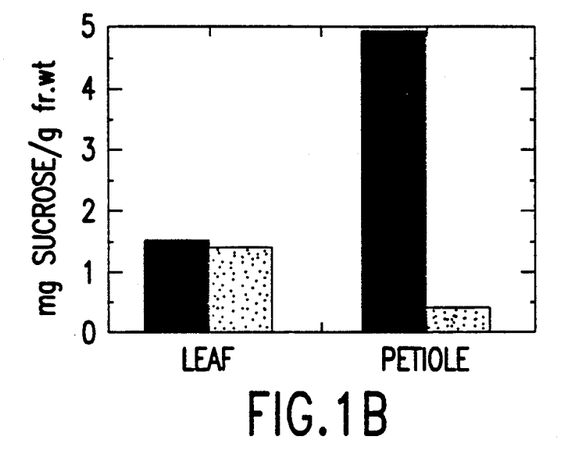
Figure 1C:
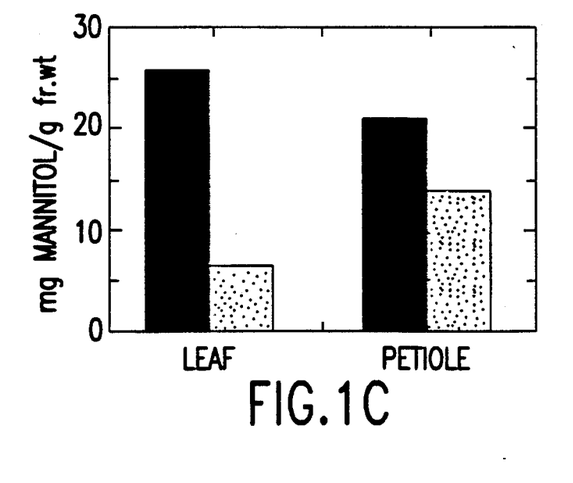
Figure 2A:
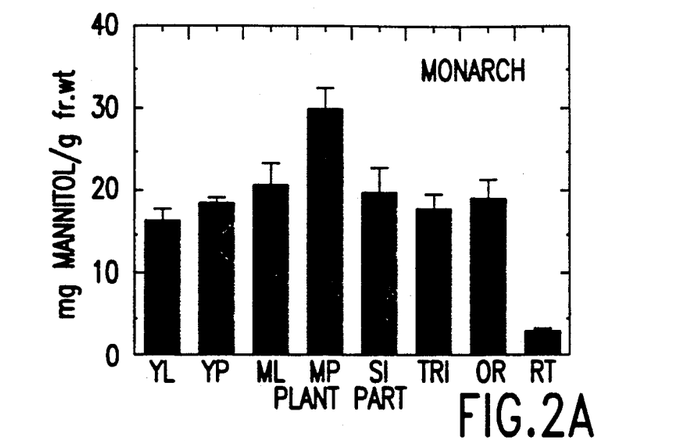
Figure 2B:
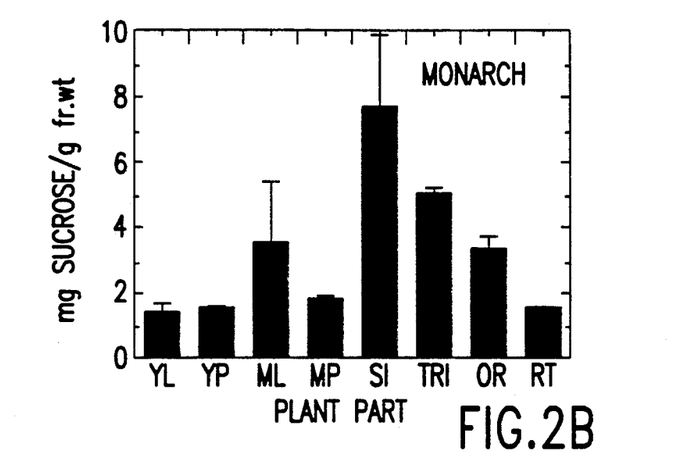
Figure 2C:
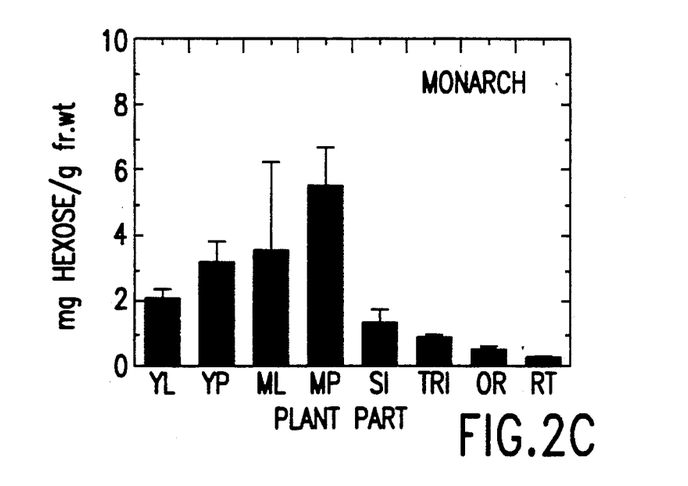

Discovery of mannitol dehydrogenase. When celeriac cv. 'Monarch' transplants were intentionally stressed for a period of four weeks by growth in seeding flats and then transplanted to 8 inch pots, both leaf and petiole hexose, sucrose and especially mannitol concentrations decreased drastically by one week after transplanting (FIG. 1). Transplants were stressed and stunted as compared to the control plants grown in 15 gallon pots in the same greenhouse environment. Total shoot weight increased only slightly over the one week period after transplanting, while root volume increased drastically (data not shown), suggesting the probability that mannitol was translocated to the root where it could be metabolized. When root tips of these stressed plants were analyzed for mannitol dehydrogenase (MDH), an activity of 7.22 μmol/h/g fresh weight (fr.wt.) was observed indicating that celeriac root tips contained a MDH which catalyzed the NAD-dependent oxidation of mannitol. No activity was observed if NADP was used as the substrate. In order to determine the tissue specificity of MDH, a crude extract of the root tip, older more fibrous root, young petiole and mature petiole of stressed celeriac transplants was analyzed for MDH activity. The highest MDH activity was observed in root tips (7.22 μmol/h/g fr.wt.). Fibrous roots, young petioles and mature petioles had a much lower activity of 1.15, 0.82 and 0.33 μmol/h/g fr.wt. respectively. When celeriac cv. 'Monarch' was grown under normal, non-stressed conditions mannitol concentration was high in the foliage, knob and older root but mannitol concentration was very low in the root tip. Foliar sucrose concentration was almost 10 fold lower as compared to mannitol concentrations and about 50% lower than the foliar hexose concentration (FIG. 2).

Figure 3:
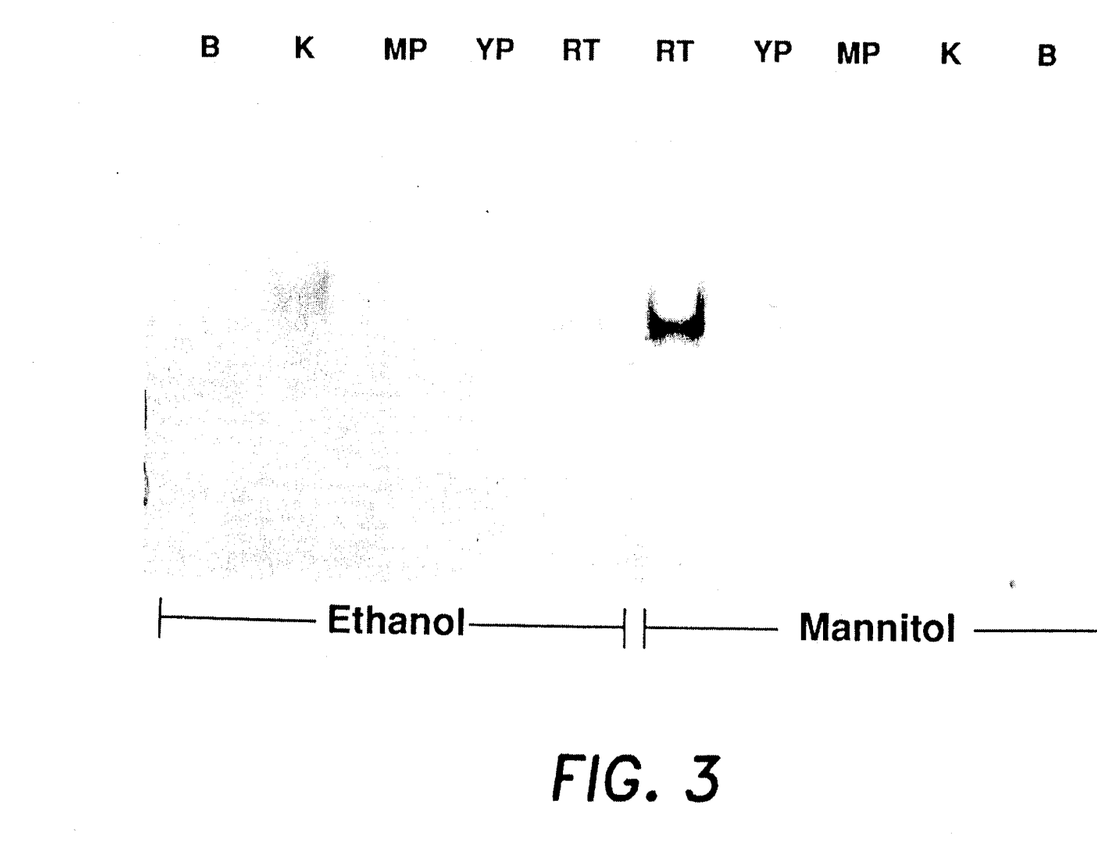
FIG. 3, left (ethanol), shows ADH activity stain of BSA (lane B), knob (lane K), mature petiole (lane MP), young petiole (lane YP) and root tip (lane RT). The right side (Mannitol) shows MDH activity stain of BSA (lane B), knob (lane K), mature petiole (lane MP), young petiole (lane YP) and root tip (lane RT). Five $\mu$l of extract was electrophoresed for each tissue.

FIG. 3 is a gel showing the MDH and ADH activity stain of different plant parts. Five μl of extract for each tissue was electrophoresed on a PAGE gel. FIG. 3 supports the previous finding that the MDH is most active in root tissue. A low activity was observed in young petioles and the knob. Alcohol dehydrogenase (ADH) activity was observed when the gel was incubated with 25 mM ethanol. The ADH activity in this 45-65% ammonium sulfate cut on the gel was lower than the MDH activity but was present in all parts of the celeriac plant. The MDH and ADH bands seemed to have a similar migration pattern, particularly in root tissue, indicating that these bands might represent a single enzyme, such as an ADH which recognizes mannitol as a substrate. Alternatively, the enzyme preparation might contain both MDH and ADH. In order to support or contradict one of these hypotheses, the MDH extract was further purified.

Purification of MDH. Ammonium sulfate fractionations were carried out at 45-65 % saturation resulting in over 100% recovery of the MDH activity and an elimination of 88% of the proteins (Table 1). It became apparent that MDH was inhibited by some substance(s) in the crude extract as indicated by the greater than 100% recovery of MDH activity.

TABLE 1

Purification table of $NAD^+$ dependent mannitol dehydrogenase

| Step | mls | Units/ ml | protein (mg/ ml) | SA (U/mg protein) | % recovery | fold purification |
|---|---|---|---|---|---|---|
| Crude Extract | 88.0 | 0.82 | 1.585 | 0.517 | 100 | — |
| $(NH_4)_2SO_4$ 45-65% saturation | 8.0 | 19.08 | 2.073 | 9.204 | 211 | 17.8 |
| Fractogel DEAE ion-exchange | 10.2 | 10.68 | 0.393 | 27.176 | 151 | 52.6 |
| $(NH_4)_2SO_4$ 90% saturation | 2.2 | 35.92 | 1.180 | 30.441 | 110 | 58.9 |

Figure 4:
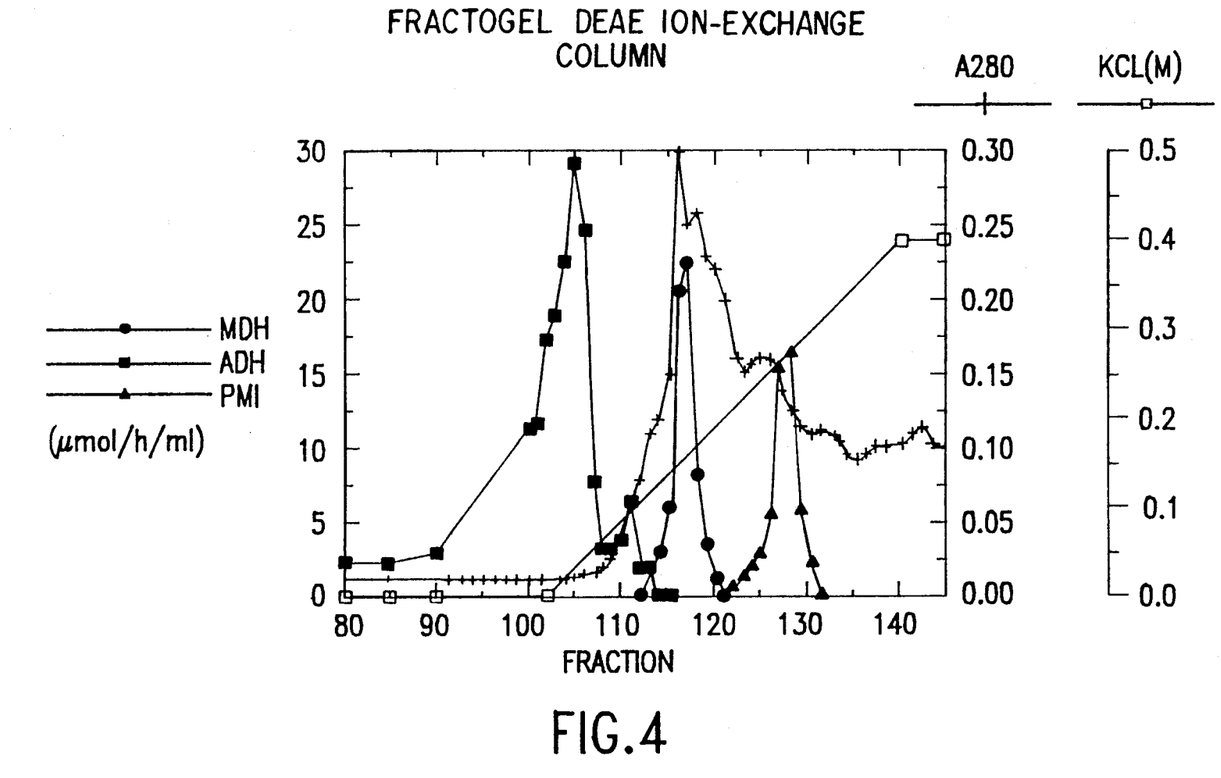
FIG. 4 shows a Fractogel DEAE ion-exchange column profile. Alcohol dehydrogenase (ADH), Mannitol dehydrogenase (MDH) and Phosphomanno isomerase (PMI) activities were analyzed. Protein content was monitored at Å 280. Proteins were eluted with a linear KCl gradient.
Figure 5A:
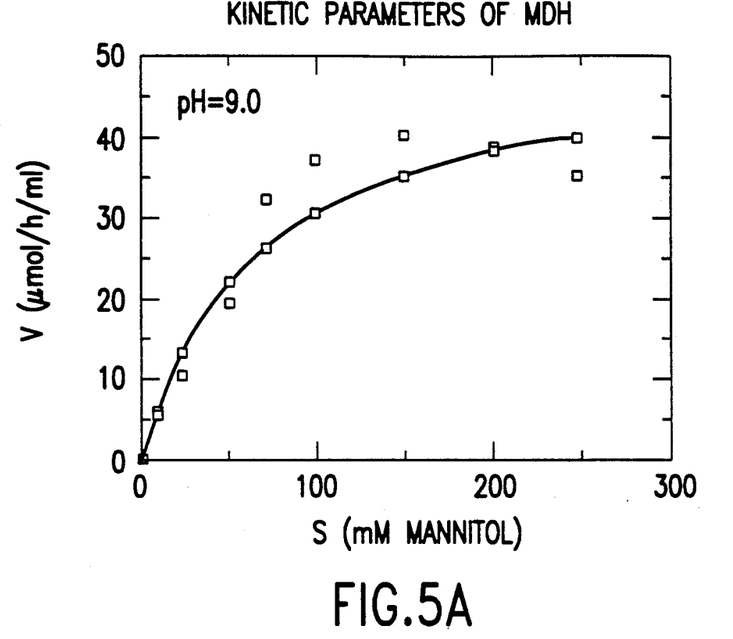
Figure 5B:
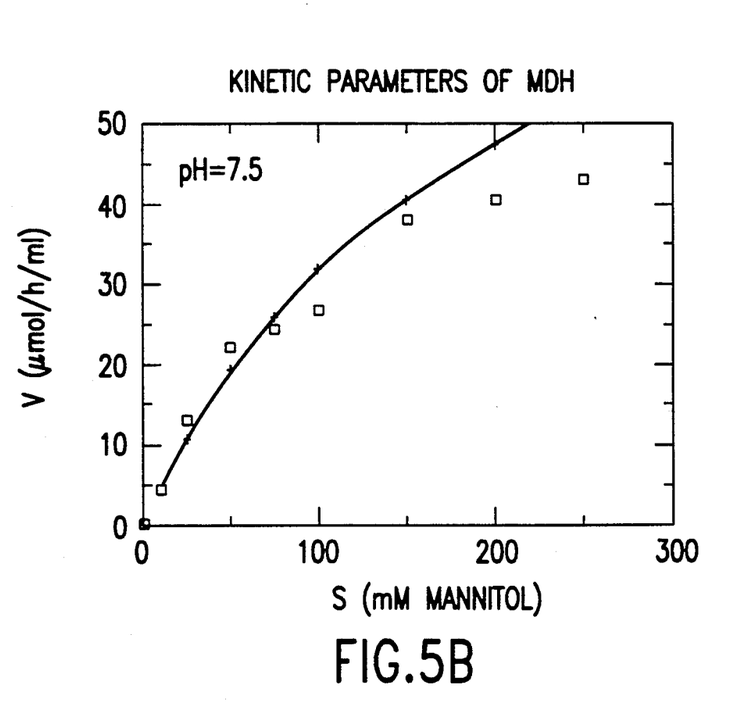
Figure 5C:
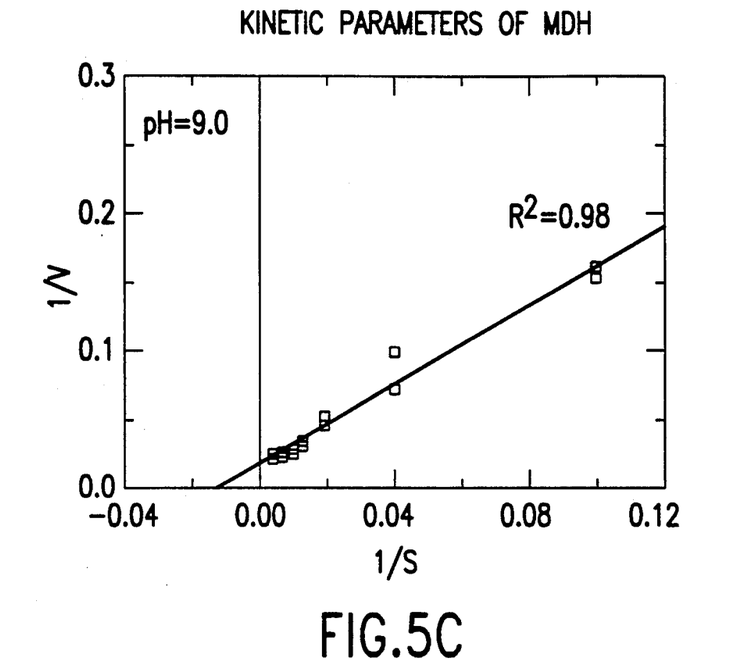
Figure 5D:
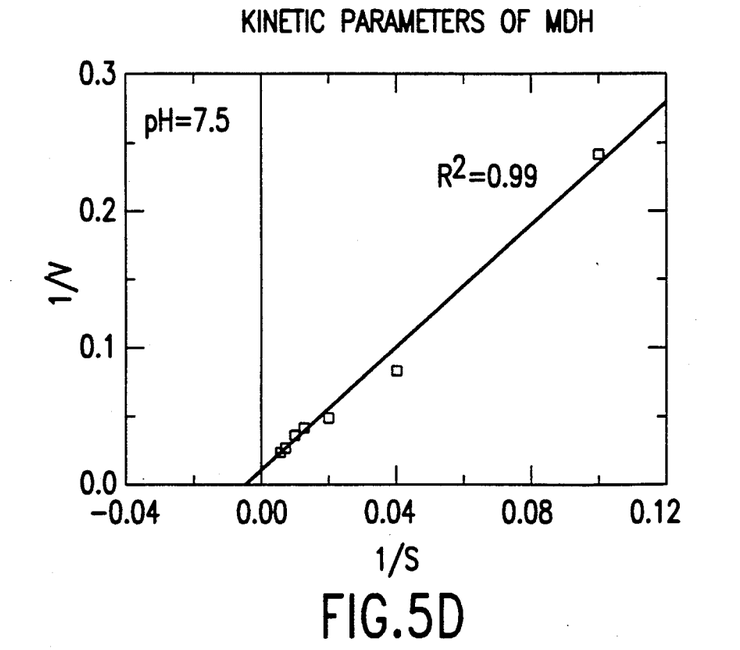
Figure 6A:
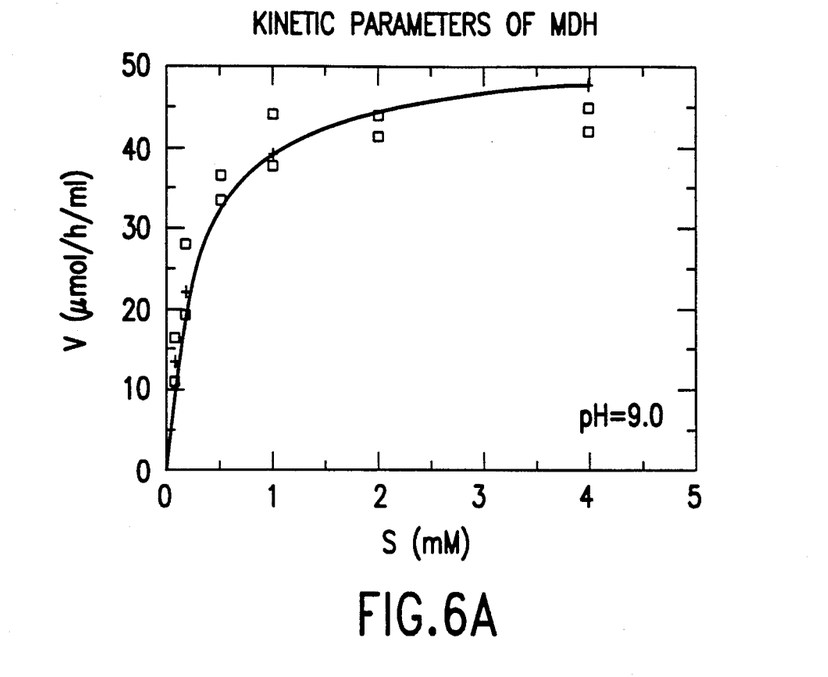
Figure 6B:
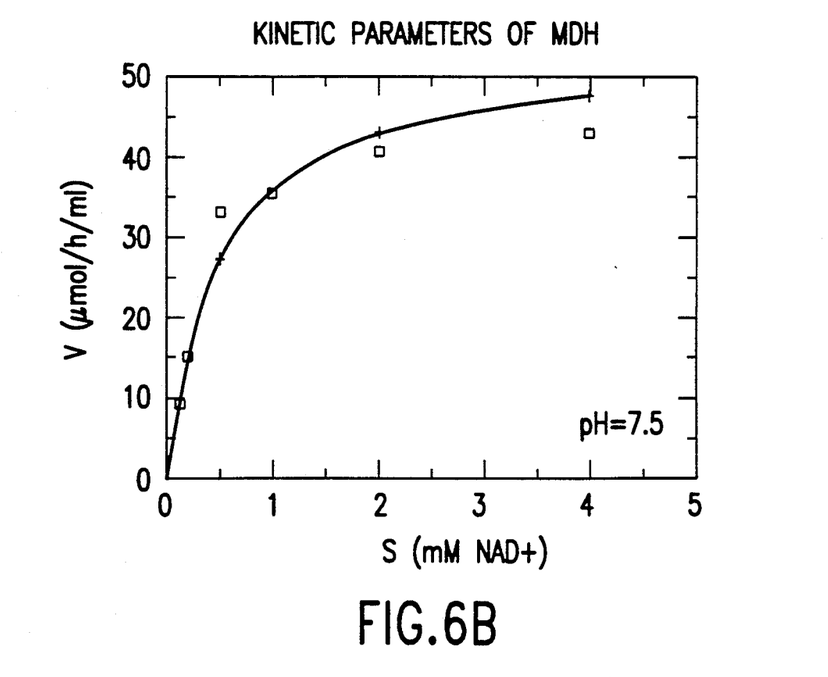
Figure 6C:
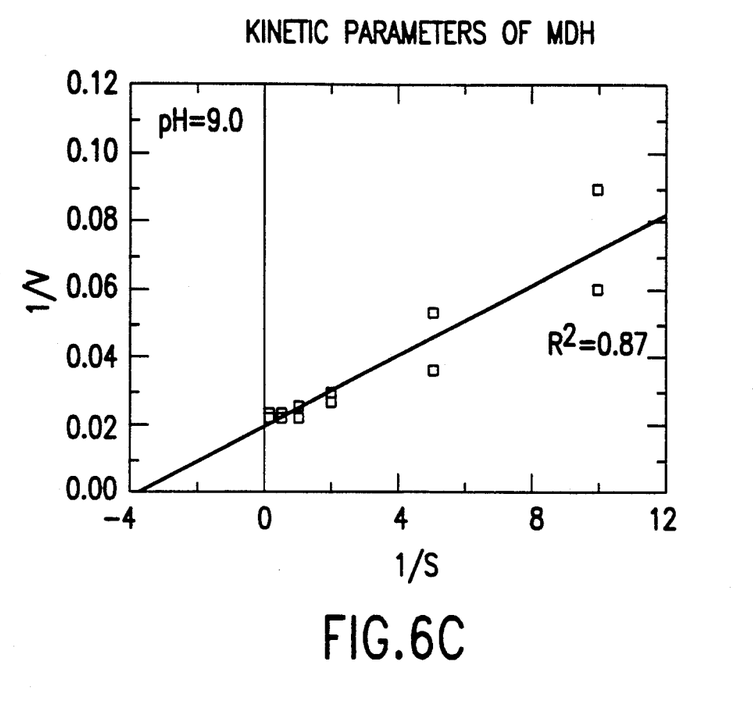
Figure 6D:
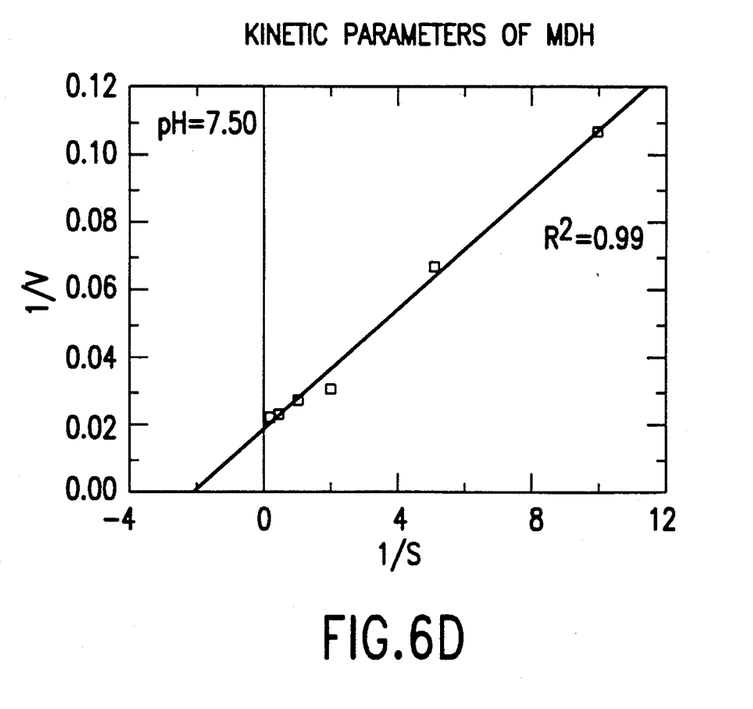

When the Fractogel® DEAE fractions were assayed for MDH, alcohol dehydrogenase (ADH) and phosphomannose isomerase (PMI) activity three distinct peaks could be observed (FIG. 4). At high protein loading, ADH was not retained on the column and eluted at the start of the salt gradient. The MDH peak eluted at 0.16 mM KCL and PMI eluted at 0.26 mM KCl. It was clear from this profile that a MDH pool could be obtained free from ADH and PMI. Purification through the DEAE step resulted in a 52-fold purification of the enzyme from the crude extract. This is, however, an apparent value, since the crude extract had inhibitory activity. The MDH pool was then concentrated with a 90% $(NH_4)_2SO_4$ saturation step resulting in a final 58-fold purification of the enzyme from the crude extract.

Product Purification and Identification. The purified MDH product resulting from the protocol described in materials and methods was analyzed on three different HPLC systems: 1) A HPLC system containing a Bio-Rad Fast Carbohydrate column (Pb column), 2) A HPLC system with high resolution conditions consisting of a Waters Sugar-Pak I calcium column and 3) A Dionex High Performance Anion Exchange Chromatography system using pulsed amperometric detection. In all three chromatographic systems the product had a retention time indistinguishable from that of reagent D-mannose and different from that of D-fructose and D-glucose (data not shown). The purified product was also identified with an enzymatic link system using commercial reagent enzymes so that the presence of mannose could be differentiated from fructose (see materials and methods). Results of the enzymatic analysis are shown in Table 2. All four independent analyses indicated that the MDH product corresponded with mannose and not fructose or glucose. Furthermore, only mannose and not fructose or glucose was reduced by MDH when assayed in the reverse direction (Table 3).

TABLE 2

Enzymatic determination of MDH product

| | $A_{340}$ | |
|---|---|---|
| Substrate | −PMI | +PMI |
| Product (±20 μg/ml) | 0.007 | 0.624 |
| Mannose std. (20 μg/ml) | 0.003 | 0.702 |
| Fructose std. (20 μg/ml) | 0.708 | 0.722 |

TABLE 3

Reverse reaction of mannitol dehydrogenase:mannose reduction

| | | pH | | |
|---|---|---|---|---|
| | | 6.0 | 7.5 | 9.0 |
| Substrate | (mM) | | μmol/h/mg protein | |
| Mannose | 20 | 0.497 | 0.810 | 0.124 |
| Fructose | 20 | na | 0.000 | na |
| Glucose | 20 | na | 0.000 | na | na: not analyzed.

Enzyme stability. The 45-65% $(NH_4)_2SO_4$ fraction could be stored overnight at 4° C. or at −80° C. for several weeks without loss of activity. The partially purified enzyme was concentrated with 90% $(NH_4)_2SO_4$ and remained stable at −80° C. for several weeks. The enzyme was always stored in the presence of 1 to 2 mM DTT.

Effect of pH on enzyme activity and kinetic constants. Initially, assays of MDH at 150 mM mannitol and 1 mM $NAD^+$ revealed that the enzyme activity was not greatly affected by variations in pH between 7.5 and 9.0. Subsequently, the effect of pH on kinetic constants, Km and Vmax, was investigated. Substrate saturation curves and Lineweaver-Burk plots with mannitol as the substrate are shown in FIG. 5. Mannitol concentrations ranged from 0 to 250 mM. Substrate saturation curves and Lineweaver-Burk plots with $NAD^+$ as the substrate are shown in FIG. 6. Kinetic parameters were based on Lineweaver-Burk plots (highest $R^2$ compared to other classic kinetic plots) and are summarized in Table 4. Normal Michaelis-Menten kinetics are exhibited for both mannitol and $NAD^+$ giving Km values of 72 mM and 0.26 mM respectively at pH=9.0. The Vmax is 40.14 μmol/h/mg protein for mannitol synthesis at pH=9.0. At pH=7.5 the substrate saturation curve for mannitol does not reach a saturating level resulting in a Km value of 228.69 mM and Vmax of 85.64 μmol/h/mg. These values are much higher than at pH=9.0 indicating that the saturating mannitol concentration at pH=9.0 is different and lower than at pH=7.5. This is also reflected in the kinetic data of NAD at pH 7.5 where a higher Km value was observed as compared to pH=9.0.

TABLE 4

Kinetic parameters of mannitol dehydrogenase

| Substrate | pH | KM (mM) | Vmax (μmol/h/mg protein) |
|---|---|---|---|
| Mannitol | 9.0 | 72.26 | 40.14 |
| $NAD+$ | 9.0 | 0.27 | 34.55 |

TABLE 4-continued

Kinetic parameters of mannitol dehydrogenase

| Substrate | pH | KM (mM) | Vmax ($\mu$mol/h/mg protein) |
|---|---|---|---|
| Mannitol | 7.5 | 228.69 | 85.64 |
| NAD+ | 7.5 | 0.46 | 35.59 |

Substrate specificity. MDH was very specific for mannitol but showed low activity with sorbitol and galactitol (Table 5). The apparent substrate specificity was higher at pH 7.5 as compared to pH 9.0. However, when a 99% pure sorbitol preparation was used at high concentration, a significant amount of contaminants could be detected by HPLC chromatography (data not shown). When sorbitol was used at 150 mM, the mannitol contamination wa high enough to contribute to the apparent oxidation of sorbitol. Therefore the actual specificity of the enzyme for mannitol might be greater than apparent from the data. NADP+ was not a substrate for activity in either the crude extract nor in the partially purified enzyme.

TABLE 5

Substrate specificity of mannitol dehydrogenase

| | | MDH ($\mu$mol/h/mg protein) | |
|---|---|---|---|
| | (mM) | pH = 7.5 | pH = 9.0 |
| Mannitol | 150 | 1.30 (100%) | 30.96 |
| Sorbitol | 150 | 3.13 (10%) | 6.77 (21%) |
| Galactitol | 75 | 1.74 (5%) | 2.20 (7%) |
| Myo-inositol | 150 | 0.00 (0%) | 0.00 (0%) |

Figure 7:
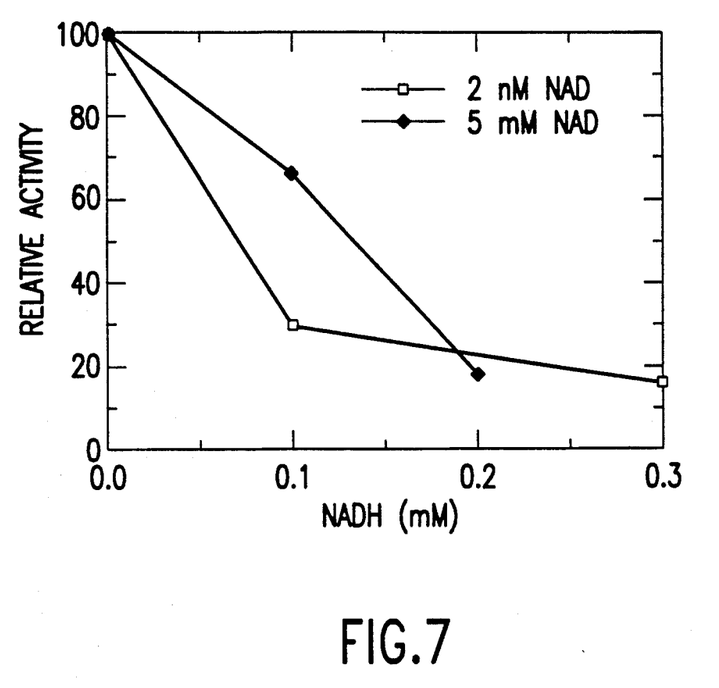
FIG. 7 shows NADH inhibition as affected by NAD concentration.

MDH effectors. When the partially purified mannitol dehydrogenase was assayed in the presence of some potential effectors such as hexose or hexose-P, no inhibition of the enzyme was observed (Table 6). The enzyme was strongly inhibited by NADH and was sensitive to alterations of NAD/NADH ratio (FIG. 7). Inorganic phosphate, PPi, ADP and ATP did not substantially affect ADH activity (Table 7). ADP may be partially inhibitory at low NAD+ concentrations.

TABLE 6

Potential Effectors of Mannitol Dehydrogenase (MDH) Activity

| Reaction Conditions | Effector | (mM) | MDH activity ($\mu$mol/h/mg prot.) | % inhibition |
|---|---|---|---|---|
| Saturating conditions (15 mM mannitol + 2 mM NAD) | — | 0 | 32.69 | — |
| | Mannose | 5 | 31.65 | 0 |
| | Sucrose | 20 | 32.68 | 0 |
| | Mannose-6-P | 5 | 36.18 | 0 |
| | Fructose-6-P | 5 | 35.83 | 0 |
| | Glucose-6-P | 5 | 32.68 | 0 |
| | Glucose-1-P | 5 | 35.83 | 0 |
| | NADH | 0.3 | 4.87 | 85 |

TABLE 7

Mannitol dehydrogenase (MDH) regulation

| Reaction conditions | Effector | (mM) | MDH activity ($\mu$mol/h/mg protein) |
|---|---|---|---|
| Saturating conditions (200 mM mannitol + 2 mM NAD) | — | 0 | 32.69 |
| | Pi | 1 | 31.65 |
| | PPi | 1 | 36.18 |
| | ADP | 1 | 35.83 |
| | ATP | 1 | 32.68 |

TABLE 7-continued

Mannitol dehydrogenase (MDH) regulation

| Reaction conditions | Effector | (mM) | MDH activity ($\mu$mol/h/mg protein) |
|---|---|---|---|
| Limiting conditions (200 mM mannitol + 0.2 mM NAD) | — | 0 | 17.39 |
| | Pi | 1 | 18.43 |
| | PPi | 1 | 20.52 |
| | ADP | 1 | 12.87 |
| | ATP | 1 | 18.79 |
| Limiting conditions (75 mM mannitol + 2 mM NAD) | — | 0 | 24.00 |
| | Pi | 1 | 25.74 |
| | PPi | 1 | 25.04 |
| | ADP | 1 | 25.04 |
| | ATP | 1 | 24.35 |

III. Summary and Conclusions

The data presented herein is the first evidence of the pressure of a mannitol oxidizing enzyme in a higher vascular plant. Based upon purification away from ADH and PMI, product identification and reverse reaction data, it is concluded that this enzyme is a NAD-dependent mannitol:mannose 1-oxidoreductase. The enzyme is not unique to celeriac but has also been found to be present in celery, *Apium graveolens* var. dulce (data not shown).

The conversion of mannitol to mannose by this plant enzyme is uniquely different from the mannitol oxidation occurring in lower organisms. Fungi, bacteria, lichens and algae oxidize mannitol to fructose either directly (N. Morton et al., *J. Gen. Microbiol.* 131:2885–2890 (1985)) or through a phosphorylated intermediate (R. Kiser et al., *Arch. Biochem. Biophys.* 211:613–621 (1981)) by a NAD+ or NADP+ dependent 2-oxidoreductase. Mannitol synthesis is also different between lower organisms and vascular plants. Celery synthesizes mannitol by a NADPH-dependent mannose-6-P reductase which reduces mannose-6-P to mannitol-1-P whereas mannitol in lower organisms is synthesized from fructose or fructose-6-P. It remains to be determined if mannitol to mannose interconversions, may occur, but have escaped detection in lower organisms.

Mannitol metabolizing plants may possess a unique advantage over non-polyol metabolizing plants in that both mannitol synthesis and mannitol utilization result in a more efficient overall metabolism. Thus, genetic transformation of plants for expression of the mannose-6-P reductase in photosynthetic tissues and the mannitol: mannose 1-oxidoreductase in sink tissues may provide a novel way to increase photosynthetic rates and biomass production in agricultural crops.

EXAMPLE 2

Affinity Purification of Mannitol Oxidoreductase

The partially purified desalted $(NH_4)_2SO_4$ 90% saturation fraction of mannitol oxidoreductase prepared as described in Example 1 above was further purified by affinity chromatography as described below.

The mannitol oxidoreductase, with a specific activity of 64.19 $\mu$mol/h/mg protein, was loaded on a $\beta$-Nicotinamide Adenine Dinucleotide agarose column (Column characteristics: Sigma N 1008, 1 ml volume, spacer 9, attachment $C_8$). The column was washed with 10 bed volumes of distilled water followed by 10 bed volumes of running buffer (RB) prior to addition of protein. (Running buffer (RB) contained: 20 mM Bis-Tris pH=9.0 and 1 mM DTT. Eluting buffer (EB) contained: 20 mM Bis-Tris pH=9.0, 2 mM NAD and 1 mM DTT). At the time of protein (partially purified mannitol:mannose 1-oxidoreductase) loading, elution solvent was collected in 1 ml fractions and the column was washed with running buffer until protein concentration in fractions (measured by A280) returned to baseline levels (approximately after 5 bed volumes). The column was then washed with eluting buffer which contained 2 mM NAD and which eluted the oxidoreductase. One ml fractions were collected and assayed for mannitol dehydrogenase (MDH) activity and protein content (Biorad method). The mannitol:mannose 1-oxidoreductase eluted in 2 ml and had a specific activity of 201 μmol/h/mg protein and a 73.79% recovery of the amount of the enzyme activity which was loaded on the column. This "NAD column" step therefore represents an additional 3.13 fold purification as compared to the "(NH4)2SO4 90% saturation" step and a 186 fold purification as compared to the crude extract (see Purification Table 7).

TABLE 7

Purification Table

| DESALTED FRACTIONS | SA(U/MG PROT)[1] | FOLD PURIFICATION |
| --- | --- | --- |
| Crude Extract | 1.079 | — |
| 45-65% (NH4)2SO4 saturation | 9.705 | 8.99 |
| Fractogel DEAE | — | — |
| 90% (NH4)2SO4 | 64.19 | 59.49 |
| NAD column | 201.00 | 186.28 |

[1]One unit (U) equals one μmol product/h.

This highly purified fraction was stored and stable at −80° C. with only a small loss (<12%) occurring during storage at −80° C.

The foregoing examples are illustrative of the present invention, and are not to be construed as limiting thereof. The invention is defined by the following claims, with equivalents of the claims to be included therein.

That which is claimed is:

1. Isolated mannitol oxidoreductase which:
  (a) is NAD+ dependent;
  (b) converts mannitol to mannose; and
  (c) is isolated from a vascular plant.

2. The mannitol oxidoreductase according to claim 1 isolated from a plant selected from the group consisting of Apiaceae, Arecaceae, Asteraceae, Brassicaceae, Bromeliaceae, Buxaceae, Cactaceae, Canellaceae, Combretaceae, Compositae, Convolvulaceae, Cucurbitaceae, Cucurbita, Euphorbiaceae, Fabaceae, Gnetaceae, Gramineae, Liliaceae, Oleaceae, Orobanchaceae, Pinaceae, Plantanaceae, Primulaceae, Punicaceae, Ranunculaceae, Rosaceae, Rubiaceae, and Scrophulariaceae.

3. The mannitol oxidoreductase according to claim 1 isolated from a plant selected from the group consisting of Apiaceae, Brassicaceae, Bromeliaceae, Compositae, Liliaceae, Oleaceae, and Rubiaceae.

4. The mannitol oxidoreductase according to claim 1 isolated from an Apiaceae.

5. The mannitol oxidoreductase according to claim 1 isolated from *Apium graveolens*.

6. The mannitol oxidoreductase according to claim 1 isolated from a plant selected from the group consisting of *Apium gravcolons* L. var. rapaceum (Mill.) Gaud. (celeriac) and *Apium graveolens* L. var. dulce (Mill.) Pers. (celery).

7. Isolated mannitol oxidoreductase which:
  (a) is NAD+ dependent;
  (b) converts mannitol to mannose; and
  (c) is isolated from coloriac.

* * * * *

UNITED STATES PATENT AND TRADEMARK OFFICE
CERTIFICATE OF CORRECTION

PATENT NO. : 5,268,288
DATED : 07 December 1993
INVENTOR(S) : David M. Pharr and Johan M.H. Stoop It is certified that error appears in the above-identified patent and that said Letters Patent is hereby corrected as shown below:

Column 1, Line 56, correct "[1>CO$_2$]" to read --[$_{14}$CO$_2$]--.

Column 3, Line 57, correct "*offinalis*" to read --*officinalis*--.

Column 10, Line 8, correct "Theextraction" to read --The extraction--.

Column 12, Line 12, correct "NAD" to read --NAD$^+$--.

Column 15, Line 41, correct "ADH" to read --MDH--.

Column 16, Line 20, correct "pressure" to read --presence--.

Column 18, Line 31, correct "gravcolons" to read --graveolens--.

Signed and Sealed this

Fifth Day of July, 1994

BRUCE LEHMAN

*Attest:*

*Attesting Officer*  *Commissioner of Patents and Trademarks*